United States Patent [19]

Ward

[11] Patent Number: 5,182,283
[45] Date of Patent: Jan. 26, 1993

[54] HETEROCYCLIC COMPOUNDS THEIR PREPARATION AND USE

[75] Inventor: John S. Ward, Indianapolis, Ind.

[73] Assignee: Novo Nordisk A/S, Bagsvaerd, Denmark

[21] Appl. No.: 669,835

[22] Filed: Mar. 15, 1991

[30] Foreign Application Priority Data

Mar. 21, 1990 [DK] Denmark .............................. 0727/90

[51] Int. Cl.$^5$ ................... A61K 31/495; C07D 401/04
[52] U.S. Cl. .................................... 514/254; 514/252; 544/405
[58] Field of Search ................ 544/405; 514/252, 254

[56] References Cited

U.S. PATENT DOCUMENTS 4,859,775 8/1989 Williams et al. ..................... 544/405

FOREIGN PATENT DOCUMENTS 327155 8/1989 European Pat. Off. .
0416754A2 3/1991 European Pat. Off. .
3048031 9/1981 Fed. Rep. of Germany ...... 544/405
1031779 2/1989 Japan .
2138179 5/1990 Japan .

OTHER PUBLICATIONS

Baker et al., Chem Abst. 112-77224q (1989).

Primary Examiner—Cecilia Tsang
Attorney, Agent, or Firm—Steve T. Zelson; Elias J. Lambiris

[57] ABSTRACT

The present invention relates to therapeutically active azacyclic or azabicyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease.

35 Claims, No Drawings

HETEROCYCLIC COMPOUNDS THEIR PREPARATION AND USE

The present invention relates to therapeutically active azacyclic or azabicyclic compounds, a method of preparing the same and to pharmaceutical compositions comprising the compounds. The novel compounds are useful as stimulants of the cognitive function of the forebrain and hippocampus of mammals and especially in the treatment of Alzheimer's disease.

Due to the in general improved health situation in the western world, elderly-related diseases are much more common now than in the past and are likely to be even more common in the future.

One of the elderly-related symptoms is a reduction of the cognitive functions. This symptom is especially pronounced in the patophysiological disease known as Alzheimer's disease. This disease is combined with, and also most likely caused by, a up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, then the postsynaptic muscarinic receptors in the forebrain and hippocampus still exist. Therefore muscarinic cholinergic $M_1$ agonists and $M_2$ antagonists are useful in the treatment of Alzheimer's disease and in improving the cognitive functions of elderly people.

It is well known that arecoline (methyl 1-methyl-1,2,5,6-tetrahydropyridine-3-carboxylate) is such a cholinergic agonist.

Arecoline however has a very short biological half life and a small separation between central and peripheral muscarinic effects. Furthermore arecoline is a rather toxic compound.

EP-A-327155 discloses a class of compounds which includes pyrazines substituted with a non-aromatic azacyclic or azabicyclic ring system which stimulate central muscarinic acetylcholine receptors and therefore are useful in the treatment of neurological and mental illnesses.

It is an object of the invention to provide new muscarinic cholinergic compounds.

The novel compounds of the invention are heterocyclic compounds having the formula I selected from the group consisting of

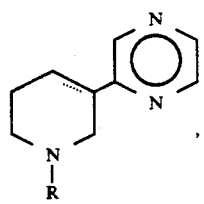
(I)

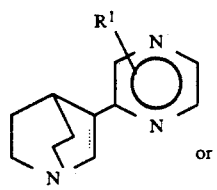
or

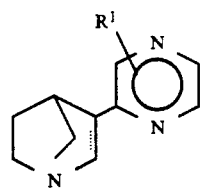

wherein R is H, $C_{1-3}$-alkyl, $C_{3-4}$-cycloalkyl, $C_{2-4}$-alkenyl or $C_{2-4}$-alkynyl and $R^1$ is straight or branched $C_{1-15}$-alkyl, straight or branched $C_{2-15}$-alkenyl, straight or branched $C_{2-15}$-alkynyl, $C_{3-7}$-cycloalkyl, $C_{4-8}$-cycloalkylalkyl, halogen, amino, $C_{1-15}$-alkylamino, $C_{1-15}$-dialkylamino, $C_{1-15}$-alkoxyamino, $S-R^2$ or $O-R^2$ wherein $R^2$ is straight or branched $C_{1-15}$-alkyl unsubstituted or substituted with one or more halogen atoms, straight or branched $C_{2-15}$-alkenyl, straight or branched $C_{2-15}$-alkynyl $C_{4-8}$-cycloalkylalkyl, $R^3$-$O$-$R^4$, $R^3$-$S$-$R^4$ wherein $R^3$ and $R^4$ independently are straight or branched $C_{1-15}$-alkyl, straight or branched $C_{2-15}$-alkenyl, straight or branched $C_{2-15}$-alkynyl,

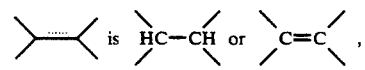

or a salt thereof with a pharmaceutically-acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salt.

The invention also relates to a method of preparing the above mentioned compounds, which comprises reacting a compound of formula II selected from the group consisting of

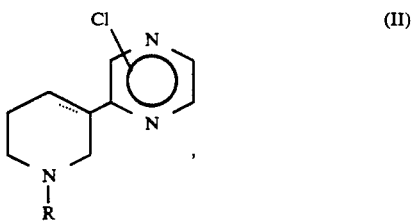
(II)

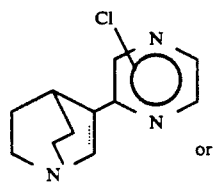
or

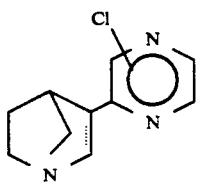

wherein R and >—< have the meanings defined above with a reactive derivative to form a compound of formula I selected from the group consisting of

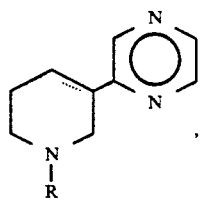   (I)

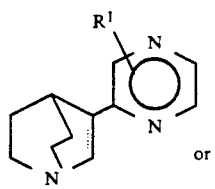 or

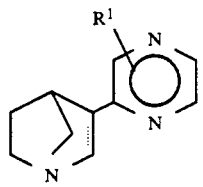

wherein R, $R^1$ and >—< have the meanings defined above.

The pharmacological properties of the compounds of the invention can be illustrated by determining their capability to inhibit the specific binding of $^3$H-Oxotremorine-M ($^3$H-Oxo).

$^3$H-Oxo labels muscarinic receptor in the CNS (with a preference for agonist domaines of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0°–4° C. unless otherwise indicated. Fresh cortex (0.1–1 g) from male Wistar rats (150–250 g) is homogenized for 5–10 s in 10 ml 20 mM Hepes pH: 7.4, with an Ultra-Turrax homogenizer. The homogenizer is rinsed with 10 ml of buffer and the combined suspension centrifuged for 15 min at 40,000×g. The pellet is washed three times with buffer. In each step the pellet is homogenized as before in 2×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 25 μl of test solution and 25 μl of $^3$H-Oxotremorine (1.0 nM, final concentration) mixed and incubated for 30 min at 25° C. Non-specific binding is determined in triplicate using arecoline (1 μg/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steambath for less than 5 minutes) at a concentration of 2.2 mg/ml. 25–75% inhibition of specific binding must be obtained before calculation of $IC_{50}$.

The test value will be given as $IC_{50}$ (the concentration (nM) of the test substance which inhibits the specific binding of $^3$H-Oxo by 50%).

$$IC_{50} = \text{(applied test substance concentration)} \times \frac{1}{\left(\frac{C_o}{C_x} - 1\right)} nM$$

where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound No. | Inhibition in vitro OXO BINDING (nM) |
|---|---|
| 3 | 17 |
| 4 | 20 |
| 5 | 99 |
| 6 | 276 |
| 13 | 72 |
| 14 | 235 |
| 15 | 4 |
| 16 | 10 |
| 17 | 18 |
| 20 | 130 |
| 21 | 5 |
| 24 | 490 |
| 25 | 6 |
| 27 | 46 |
| 28 | 5.6 |
| 34 | 19 |
| 36 | 13 |
| 37 | 23 |
| 38 | 9 |
| 39 | 0.7 |
| 40 | 2 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective muscarinic cholinergic agonistic amount of the active ingredient commensurate with the intended daily dosage range to be employed. Tablets containing ten (10) milligrams of the active ingredient or, more broadly, one (1) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for Oral application. A syrup, elixir of the like can be used in cases where a sweetened vehicle can be employed.

Generally, the compounds of this invention are dispensed in unit form comprising 1-100 mg in a pharmaceutically acceptable carrier per unit dosage.

The dosage of the compounds according to this invention is 1-100 mg/day, preferably 10-70 mg/day, when administered to patients, e.g. humans, as a drug.

A typical tablet which may be prepared by conventional tabletting techniques contains:

| Active compound | 5.0 mg |
|---|---|
| Lactosum | 67.8 mg Ph.Eur. |
| Avicel ® | 31.4 mg |
| Amberlite ® | 1.0 mg |
| *Magnesii stearas* | 0.25 mg Ph.Eur. |

Due to the high muscarinic cholinergic receptor agonistic activity, the compounds of the invention are extremely useful in the treatment symptoms related to a reduction of the cognitive functions of the brain of mammals, when administered in an amount effective for stimulating the cognitive functions of the forebrain and hippocampus. The important stimulating activity of the compounds of the invention includes both activity against the patophysiological disease, Alzheimer's disease as well as against normal degeneration of brain function. The compounds of the invention may accordingly be administered to a subject, e.g., a living animal body, including a human, in need of stimulation of the cognitive functions of the forebrain and hippocampus, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective forebrain and hippocampus stimulating amount, and in any event an amount which is effective for improving the cognitive function of mammals due to their muscarinic cholinergic receptor agonistic activity. Suitable dosage ranges are 1-100 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

Elemental analysis are indicated only by the symbols of the elements after the empirical formula and are within 0.4% of the theoretical values. Melting points were determined on a Mel-Temp apparatus and are uncorrected. HPLC separations were performed on a Waters PrepLC/500A using PrepPAK-500 silica gel cartridges with the solvents specified. Radial chromatography was performed on a Chromatotron Model 7924T using Analtech Precast Rotors made of Silica Gel GF and eluting with the solvents specified. TLC was carried out on Merck F254 silica gel plates. All reactions, exclusive of extraction procedures, were conducted under an Ar atmosphere. NMR measurements were made with a QE300 using the solvents described.

The invention will now be described in further detail with reference to the following examples:

EXAMPLE 1

3-(3-Chloropyrazinyl)-1-methyl-3-piperidinol (1)

A solution of 7.2 ml 2,2,6,6-tetramethylpiperidine (0.034 mol) in 300 ml of dry THF was cooled to −8° C. as 25 ml of 1.6 M butyllithium (0.04 mol) in hexane was added dropwise. The reaction was stirred 20 min then cooled to −77° C. A solution of 2.9 ml of 2-chloropyrazine (0.031 mol) in 5 ml of THF was added dropwise to the reaction. After another 15 min, 3.5 g of 1-methylpiperidin-3-one (0.035 mol) in 10 ml of THF was added dropwise. After the addition, the reaction was stirred 1.5 h followed by addition of a mixture of 8 ml of concentrated HCl and 4 ml of ethanol. The cooling was removed and when the temperature had reached −15° C., 20 ml of 5 N NaOH was added. The volatile organics were evaporated and the aqueous residue was extracted 4× with 30 ml of $CH_2Cl_2$. The extracts were washed with brine, dried and the solvent evaporated to give a brown solid that was dissolved in 300 ml of ether and filtered. The ether was evaporated and the residue recrystallized from hexane to give 3.77 g of (1), 53% yield, mp 111°-112° C. NMR ppm (CDCl$_3$) 1.7-2.2 (5H,m), 2.4 (3H, s), 2.7 (1H, d), 2.85-3.05 (2H, m), 4.4 (1H, bs), 8.35 (1H, d), 8.5 (1H, d). Anal. $C_{10}H_{14}ClN_3O$, requires C: 52.75; H: 6.20; N: 18.46%. Found C: 52.64; H: 6.21; N: 18.21%.

3-(3-Methoxypyrazinyl)-1,2,5,6-tetrahydro-1-methylpyridine ethandioate (2)

A mixture of 0.32 g of (1) (0.0014 mol) and 10 ml of thionyl chloride was heated to reflux for 1.5 h. The excess thionyl chloride was evaporated, the residue treated with ice-water and made basic with saturated aqueous $K_2CO_3$. The mixture was extracted 3× with 25 ml of $CH_2Cl_2$, the extracts washed with brine, dried, and the solvent evaporated. The residue was dissolved in 5 ml of methanol and added to 25 ml of methanol that had reacted with 0.35 g of Na (0.015 mol). The reaction was heated to reflux for 1.5 h. The solvent was evaporated, the residue was treated with ice-water and the mixture extracted 3× with 25 ml of $CH_2Cl_2$. The extracts were washed with brine, dried, and the solvent evaporated to give a dark liquid, 0.15 g. The liquid was dissolved in ethyl acetate and treated with oxalic acid to give 0.05 g of (2) after recrystallization from ethyl acetate, mp 150°–151° C. NMR ppm ($D_2O$) 2.6–2.9 (2H, m), 3.1 (3H, s), 3.3 (1H, m), 3.65 (1H, m), 4.0 (3H, s), 4.05 (1H, dd), 4.35 (1H, d), 6.95 (1H, bs), 8.07 (1H, d), 8.1 (1H, d). Anal. $C_{11}H_{15}N_3O \cdot C_2H_2O_4$ requires C: 52.88; H: 5.80; N: 14.23%. Found C: 52.66; H: 5.94; N: 14.04%.

3-(3-Butyloxypyrazinyl)-1,2,5,6-tetrahydro-1-methylpyridine ethanedioate (3)

A mixture of 0.5 g of (1) (0.0022 mol) and 10 ml of thionyl chloride was stirred for 1.5 h. The solvent was evaporated, the residue treated with ice-water, and the mixture made basic with saturated aqueous $K_2CO_3$. The mixture was extracted 3× with 25 ml of $CH_2Cl_2$, the extracts washed with brine, dried, and the solvent evaporated. The residue was dissolved in a small amount of butanol and added to 25 ml of butanol that had reacted with 0.5 g of Na (0.022 mol). The reaction was heated to reflux for 2.5 h. After evaporation of the solvent, the residue was treated with ice-water and 3 ml of concentrated HCl. The mixture was extracted 2× with ether. The aqueous solution was made basic with 5 N NaOH, extracted 3× with 25 ml of $CH_2Cl_2$, the extracts washed with brine, dried, and the solvent evaporated. The brown liquid residue was purified by HPLC eluting with an 8 L gradient starting with $CH_2Cl_2$ and going to 10% methanol to give 0.1 g of a yellow liquid. The oxalate salt (3), 0.08 g, crystallized from ethyl acetate, mp 160°–161.5° C. NMR of the free base, ppm ($CDCl_3$) 1.0 (3H, t), 1.55 (2H, m) 1.85 (2H, m), 2.5 (5H, bs+s), 2.63 (2H, t), 3.5 (2H, m), 4.4 (2H, t), 7.1 (1H, m), 7.9 (1H, d), 8.1 (1H, d). Anal. $C_{14}H_{21}N_3O \cdot C_2H_2O_4$ requires C: 56.96; H: 6.87; N: 12.45%. Found C: 56.59; H: 7.12; N: 12.34%.

3-(3-Hexyloxypyrazinyl)-1,2,5,6-tetrahydro-1-methylpyridine diethanoate (4)

A mixture of 0.75 g of (1) (0.0033 mol) and 5 ml of thionyl chloride was stirred for 1 h followed by evaporation of the solvent. The residue was treated with ice-water, made basic with saturated aqueous $K_2CO_3$, and extracted 3× with $CH_2Cl_2$. The extracts were washed with brine, dried, and the solvent evaporated. The residue was dissolved in a small amount of hexanol and added to 25 ml of hexanol that had reacted with 0.5 g of Na (0.022 mol). The reaction was heated to 120° C. for 2 h followed by evaporation of the solvent. The residue was treated with 10 ml of 5 N HCl and the remaining hexanol was azeotroped off with water. The residue was made basic with 5 N NaOH and extracted 3× with 25 ml of $CH_2Cl_2$. The extracts were washed with brine, dried, and the solvent evaporated. The residue was purified by HPLC eluting with an 8 L gradient starting with $CH_2Cl_2$ and going to 10% methanol-1% $NH_4OH$ to give 0.32 g of brown liquid. The oxalate salt (4), 0.34 g, crystallized from ethyl acetate, mp 154°–155° C. NMR of the free base, ppm ($CDCl_3$) 0.95 (3H, t), 1.3–1.55 (6H, m), 1.85 (2H, m), 2.5 (5H, bs+s), 2.65 (2H, t), 4.4 (2H, t), 7.1 (1H, m), 7.9 (1H, d), 8.1 (1H, d). Anal. $C_{16}H_{25}N_3O \cdot C_2H_2O_4$ requires C: 59.16; H: 7.45; N: 11.50%. Found C: 58.91; H: 7.34; N: 11.26%.

3-(3-(2-Methoxyethoxy)pyrazinyl)-1,2,5,6-tetrahydro-1-methylpyridine ethanedioate (5)

A mixture of 0.8 g of (1) (0.0035 mol) and 6 ml of thionyl chloride was stirred for 1 h followed by evaporation of the solvent. The residue was treated with ice-water, made basic with saturated aqueous $K_2CO_3$, and extracted 3× with 25 ml of $CH_2Cl_2$. The extracts were washed with brine, dried, and the solvent evaporated. The residue was dissolved in a small amount of 2-methoxyethanol and added to 25 ml of 2-methoxyethanol that had reacted with 0.5 g of Na (0.022 mol). The reaction was heated to 100° C. for 2 h, followed by evaporation of the solvent. The residue was treated with ice-water and extracted 3× with 25 ml of $CH_2Cl_2$. The extracts were washed with brine, dried, and the solvent evaporated. The residue was purified by HPLC eluting with an 8 L gradient starting with $CH_2Cl_2$ and going to 10% methanol to give 0.31 g of a yellow liquid. The oxalate salt (5), 0.26 g, crystallized from ethyl acetate, mp 149.5°–150.5° C. NMR of the free base, ppm ($CDCl_3$) 2.5 (5H, bs+s), 2.65 (2H, t), 3.45 (3H, s), 3.5 (2H, m), 3.8 (2H, t), 4.55 (2H, t), 7.15 (1H, m), 7.9 (1H, d), 8.1 (1H, d). Anal. $C_{13}H_{19}N_3O_2 \cdot C_2H_2O_4$ requires C: 53.09; H: 6.24; N: 12.38%. Found C: 53.09; H: 6.29; N: 12.37%.

3-(3-Chloropyrazinyl)-1,2,5,6-tetrahydro-1-methylpyridine ethanedioate (6)

A solution of 10 ml of thionyl chloride was cooled to 0° C. as 1 g of (1) (0.0044 mol) was added. Cooling was removed and the reaction stirred 2 h. The solvent was evaporated, the residue treated with ice-water, and the mixture made basic with saturated aqueous $K_2CO_3$. The mixture was extracted 3× with 25 ml of $CH_2Cl_2$, extracts washed with brine, dried, and the solvent evaporated. The residue was purified by HPLC eluting with an 8 L gradient starting with $CH_2Cl_2$ and going to 7.5% methanol-1% $NH_4OH$ to give 0,43 g of an orange liquid. The oxalate salt (6), 0.26 g, crystallized from isopropanol, mp 110°–111° C. NMR ppm ($D_2O$) 2.75 (2H, m), 3.05 (3H, s), 3.35 (1H, m), 3.65 (1H, m), 4.05 (1H, m), 4.25 (1H, d), 6.62 (1H, bs), 8.38 (1H, d), 8.55 (1H, d). Anal. $C_{10}H_{12}ClN_3 \cdot C_2H_2O_4$ requires C: 48.09; H: 4.71; N: 14.02%. Found C: 48.06; H: 4.76; N: 13.86%.

3-(3-Heptyloxypyrazinyl)-1,2,5,6-tetrahydro-1-methylpyridine ethanedioate (17)

A mixture of 0.9 g of (1) (0.0039 mol) and 6 ml of thionyl chloride was stirred for 1 h followed by evaporation of the solvent. The residue was treated with ice-water, made basic with saturated aqueous K and extracted 3× with 25 ml of $CH_2Cl_2$. The extracts were washed with brine, dried, and the solvent evaporated. The residue was dissolved in a small amount of heptanol and added to 35 ml of heptanol that had reacted with 0.5 g of Na (0.022 mol). The reaction was heated to 100° C. for 2 h, cooled to ambient temperature and treated with 6 ml of 5N HCl. The heptanol was azeotroped off with water the aqueous residue made basic with saturated aqueous $K_2CO_3$ and then extracted 3× with 25 ml of $CH_2Cl_2$. The extracts were washed with brine, dried, and the solvent evaporated. The residue was purified by HPLC eluting with an 8 L gradient starting with $CH_2Cl_2$ and going to 10% methanol to give 0.43 g of yellow liquid that crystallized from ethyl acetate as the oxalate salt (17), 0.41 g, mp 125°–127° C. NMR of free base, ppm ($CDCl_3$) 0.9 (3H, t), 1.22–1.52 (8H, m), 1.82

(2H, m), 2.5 (5H, bs), 2.62 (2H, t), 3.5 (2H, m), 4.4 (2H, t), 7.1 (1H, m), 7.9 (1H, d), 8.05 (1H, d). Anal. $C_{17}H_{27}N_3O \cdot C_2H_2O_4$ requires C: 60.14; H: 7.70; N: 11.07%. Found C: 59.92; H: 7.61; N: 10.94%.

3-(3-Ethoxypyrazinyl)-1,2,5,6-tetrahydro-1-methylpyridine ethandioate (32)

A mixture of 1.1 g (0.0048 mol) of 3-(3-chloropyrazinyl)-1-methyl-3-piperidinol (1) and 7 ml of thionyl chloride was stirred for 1 h at ambient temperature. Excess thionyl chloride was evaporated, the residue was treated with ice-water, and the solution made basic with 5N NaOH. The mixture was extracted 3× with 25 ml of $CH_2Cl_2$, the extracts dried, and the solvent evaporated. The residue was dissolved in 5 ml of anhydrous ethanol and added to a solution of sodium ethoxide prepared from 0.7 g (0.03 mol) of sodium and 35 ml of anhydrous ethanol. The solution was heated to reflux for 2 h, the reaction cooled to ambient temperature, and 5 ml of water was added. The solvents were evaporated, the residue dissolved in water, and the mixture extracted 3× with 25 ml of $CH_2Cl_2$. The extracts were dried and the solvent was evaporated. The residue was purified by radial chromatography eluting with 5% ethanol/0.5% $NH_4OH/CHCl_3$ and the desired product converted to the oxalate salt (32), that crystallized from ethyl acetate with 0.25 mol of water, 0.55 g, 38% yield, mp 133°-135° C. NMR ppm($CDCl_3$) 1.45 (3H, t), 2.62 (1H, bm), 2.75-3.2 (5H, m), 3.5-3.95 (2H, m), 4.3-4.75 (3H, m), 4.8-5.3 (2H, m), 7.38 (1H, m), 7.98 (1H, d), 8.05 (1H, d). Anal. $C_{12}H_{17}N_3O \cdot C_2H_2O_4 \cdot 0.25 H_2O$ requires C: 53.58; H: 6.26; N: 13.39%. Found C: 53.80; H: 6.15; N: 13.08%.

3-(3-Propyloxypyrazinyl)-1,2,5,6-tetrahydro-1-methylpyridine ethandioate (33)

A mixture of 1 g (0.0044 mol) of (1) and 7 ml of thionyl chloride was stirred 1 h, the excess thionyl chloride was evaporated, and the residue was treated with ice-water. The solution was made basic with 5 N NaOH and the mixture extracted 3× with 25 ml of $CH_2Cl_2$. The solvent was evaporated from the dried extracts, the residue dissolved in 5 ml of 1-propanol, and the solution added to a solution of sodium propoxide prepared from 0.7 g (0.03 mol) of sodium and 35 ml of 1-propanol. The mixture was heated to reflux for 2 h, the reaction was cooled to ambient temperature, 5 ml of water added, and the solvents evaporated. The residue was treated with water and extracted 3× with 25 ml of $CH_2Cl_2$. The extracts were dried and the solvent evaporated to give a brown liquid that was purified by radial chromatography eluting with 5% ethanol/0.5% $NH_4OH/CHCl_3$. The oxalate salt (33) crystallized from ethyl acetate to give 0.38 g, 27% yield, of white solid, mp 146°-147° C. NMR ppm($CDCl_3$) 1.05 (3H, t), 1.87 (2H, m), 2.75-2.92 (2H, m), 3.0 (3H, s), 3.2-3.55 (2H, m) 4.0-4.4 (4H, m), 7.38 (1H, m), 7.97 (1H, d), 8.06 (1H, d). Anal. $C_{13}H_{19}N_3O \cdot C_2H_2O_4$ requires C: 55.72; H: 6.56; N: 12.99%. Found C: 55.52; H: 6.42; N: 13.02%.

3-(3-Pentyloxypyrazinyl)-1,2,5,6-tetrahydro-1-methylpyridine ethandioate (34)

A mixture of 1 g (0.0044 mol) of (1) and 7 ml of thionyl chloride was stirred 1 h, the excess thionyl chloride was evaporated, and the residue was treated with ice-water. The solution was made basic with 5 N NaOH and the mixture extracted 3× with 25 ml of $CH_2Cl_2$. The solvent was evaporated from the dried extracts, the residue was dissolved in 5 ml of 1-pentanol, and the solution added to a solution of sodium pentoxide prepared from 0.7 g (0.03 mol) of sodium and 35 ml of 1-pentanol. After heating at 100° C. for 2 h, the reaction was cooled to ambient temperature, 35 ml of 1N HCl was added and the excess pentanol evaporated. The residue was dissolved in water, the solution made basic with 5 N NaOH, and the mixture extracted 3× with 25 ml of $CH_2Cl_2$. The solvent was evaporated from the dried extracts and the residue purified by radial chromatography eluting with 5% ethanol/0.5% $NH_4OH/CHCl_3$. The oxalate salt (34), 0.52 g, 34% yield crystallized from ethyl acetate, mp 151°-152° C. NMR ppm-($CDCl_3$) 0.94 (3H, t), 1.43 (4H, m), 1.84 (2H, m), 2.7-2.9 (2H, m), 2.99 (3H, s), 3.2-3.55 (2H, m), 4.0-4.43 (4H, m), 7.38 (1H, m), 7.97 (1H, d), 8.06 (1H, d). Anal. $C_{15}H_{23}N_3O \cdot C_2H_2O_4$ requires C: 58.11; H: 7.17; N: 11.96%. Found C: 57.93; H: 7.20; N: 12.09%.

3-(3-Hexylthiopyrazinyl)-1,2,5,6-tetrahydro-1-methylpyridine hydrochloride (35)

A mixture of 1.1 g (0.0048 mol) of (1) and 7 ml of thionyl chloride was stirred 1 h, the excess thionyl chloride was evaporated, and the residue was treated with ice-water. The solution was made basic with 5 N NaOH and the mixture extracted 3× with 25 ml of $CH_2Cl_2$. The solvent was evaporated from the dried extracts, the residue was dissolved in 10 ml of THF, and the solution was added to a suspension of sodium hexylthiolate in THF prepared from 0.21 g (0.0091 mol) NaH, 2 ml (0.014 mol) hexanethiol, and 30 ml of THF. The reaction was heated to reflux for 20 min followed by distillation of most of the THF from the reaction mixture. The solvents were evaporated, the residue treated with water, and the mixture extracted 3× with 25 ml of $CH_2Cl_2$. The solvent was evaporated from the dried extracts and the residue purified by radial chromatography eluting with 5% ethanol/0.5% $NH_4OH/CHCl_3$. The hydrochloride salt (35), 0.33 g, 21% yield crystallized from ethyl acetate as a white solid, mp 120.5°-122° C. NMR ppm($CDCl_3$) 0.9 (3H,t), 1.31 (4H, m), 1.44 (2H, m), 1.67 (2H, m), 2.6-2.7 (1H, m), 2.96 (3H, d), 3.05-3.22 (4H, m), 3.54-3.64 (1H, m), 3.72-3.8 (1H, m), 4.4-4.45 (1H, d), 6.8 (1H, m), 8.15 (1H, d), 8.28 (1H, d). Anal. $C_{16}H_{25}N_3S \cdot HCl$ requires C: 58.61; H: 7.99; N: 12.81%. Found C: 58.48; H: 7.93; N: 12.84%.

3-(3-Pentylthiopyrazinyl)-1,2,5,6-tetrahydro-1-methylpyridine hydrochloride (36)

A mixture of 1 g (0.0044 mol) of (1) and 7 ml of thionyl chloride was stirred 1 h, the excess thionyl chloride was evaporated, and the residue was treated with ice-water. The solution was made basic with 5 N NaOH and the mixture extracted 3× with 25 ml of $CH_2Cl_2$. The solvent was evaporated from the dried extracts, the residue was dissolved in 10 ml of THF, and the solution was added to a suspension of sodium hexylthiolate in THF prepared from 0.18 g (0.0078 mol) NaH, 2 ml (0.016 mol) pentanethiol, and 30 ml of THF. The reaction was heated to reflux for 20 min followed by distillation of most of the THF from the reaction mixture. The solvents were evaporated, the residue treated with water, and the mixture extracted 3× with 25 ml of $CH_2Cl_2$. The solvent was evaporated from the dried extracts and the residue purified by radial chromatography eluting with 5% ethanol/0.5% $NH_4OH/CHCl_3$. The hydrochloride salt (36), 0.26 g, 19% yield crystallized from ethyl acetate as colorless crystals, mp 123°–124° C. NMR ppm (CDCl$_3$) 0.9 (3H, t), 1.38 (4H, m), 1.7 (2H, m), 2.58–2.7 (1H, m), 3.0 (3H, d), 3 05–3.2 (4H, m), 3.5–3.6 (1H, m), 3.7–3.82 (1H, m), 4.4–4.47 (1H, d), 6.8 (1H, m), 8.15 (1H, d), 8.28 (1H, d). Anal. C$_{15}$H$_{23}$N$_3$S·HCl requires C: 57.40; H: 7.71; N: 13.37%. Found C: 57.43; H: 7.63; N: 13.45%.

EXAMPLE 2

3-(3-Chloropyrazinyl)-1-azabicyclo[2.2.2]octan-3-ol (7)

A solution of 7.2 ml 2,2,6,6-tetramethylpiperidine (0.034 mol) in 300 ml of dry THF was cooled to −8° C. as 25 ml of 1.6 M butyllithium (0.04 mol) in hexane was added dropwise. The reaction was stirred 20 min then cooled to −77° C. A solution of 2.9 ml of 2-chloropyrazine (0.031 mol) in 5 ml of THF was added dropwise to the reaction dropwise. After 15 min, 4.4 g of 3-quinuclidinone (0.0352 mol) in 5 ml of THF was added dropwise and the reaction stirred another 1.5 h. A solution of 8 ml of concentrated HCl and 4 ml of ethanol was added and the cooling was removed. When the temperature reached −5° C., 20 ml of 5 N NaOH was added and the volatile organics were evaporated. The residue was suspended in 50 ml of ice-water and the mixture filtered. The aqueous filtrate was extracted 3× with 50 ml of CHCl$_3$. The extracts were combined with the solid collected from the filtration and the volume of the mixture adjusted to 450 ml with additional CHCl$_3$. The mixture was heated on a steam bath until most of the solid had dissolved. The mixture was dried, filtered, and the solvent evaporated to give a dark brown solid that was recrystallized from isopropanol to give 6.3 g of (7), mp 215°–216° C. NMR ppm (CDCl$_3$) 1.25(1H, m), 1.5 (2H, m), 2.2 (1H, m), 2.65–3.1 (6H, m), 3.6 (1H, bs), 4.05 (1H, d), 8.3 (1H, d), 8.5 (1H, d). Anal. C$_{11}$H$_{14}$ClN$_3$O requires C: 55.12; H: 5.89; N: 17.53%. Found C: 55.21; H: 5.99; N: 17.30%.

3-(3-Methoxypyrazinyl)-1-azabicyclo[2.2.2]octan-3-ol (8)

To a solution of 40 ml of methanol that had reacted with 0.5 g of Na (0.022 mol) was added 0.5 g of (7) (0.0021 mol). The reaction was heated to reflux for 1 h followed by evaporation of the solvent. The residue was treated with ice-water and extracted 3× with 25 ml of CH$_2$Cl$_2$. The extracts were dried and evaporated to give a yellow solid that was recrystallized from ethyl acetate to give (8), 0.12 g, mp 130°–131° C. NMR ppm (CDCl$_3$) 1.15 (1H, m), 1.45 (2H, m), 2.25 (1H, m), 2.38 (1H, m), 2.7–3.15 (5H, m), 3.9 (1H, bs), 4.05 (3H, s), 4.3 (1H, d), 8.05 (1H, d), 8.15 (1H, d). Anal. C$_{12}$H$_{17}$N$_3$O$_2$ requires C: 61.26; H: 7.28; N: 17.86%. Found C: 61.02; H: 7.45; N: 17.95%.

Alternate Synthesis of (8)

A solution of 5.4 ml of 2,2,6,6-tetramethylpiperidine, in 300 ml of dry THF was cooled to −8° C. as 19 ml of 1.6 M butyllithium (0.03 mol) in hexane was added dropwise. The reaction was stirred 20 min then cooled to −77° C. A solution of 2.5 g of 2-methoxypyrazine (0.023 mol) in 5 ml of THF was added dropwise to the reaction. After 5h, 2.9 g of 3-quinuclidinone (0.023 mol) in 5 ml of THF was added dropwise and the reaction stirred another h. A solution of 8 ml of concentrated HCl and 4 ml of ethanol was added, the cooling was removed, and when the temperature reached −10° C., 20 ml of 5 N NaOH was added. The volatile organics were evaporated and the residue extracted 3× with 50 ml of CHCl$_3$. The extracts were washed with brine, dried, and the solvent evaporated to give a clear yellow liquid that solidified on further drying. Recrystallization from ether gave 3.53 g of (8) identical to the material produced in the previous reaction.

3-Chloro-3-(3-chloropyrazinyl)-1-azabicyclo[2.2.2]octane (9) and 3-(3-chloropyrazinyl)-1-azabicyclo[2.2.2]oct-2-ene (10)

A solution of 12 ml of thionyl chloride was cooled to 0° C. as 1 g of (7) (0.0042 mol) was added. The cooling was removed and the reaction stirred overnight. The solvent was evaporated, the residue was treated with ice-water, and the mixture made basic with saturated aqueous K$_2$CO$_3$. The mixture was extracted 3× with 25 ml of CH$_2$Cl$_2$ the extracts washed with brine, dried, and the solvent evaporated. The residue was purified by HPLC eluting with an 8 L gradient beginning with CH$_2$Cl$_2$ and going to 10% methanol-1%NH$_4$OH. Compound (9), 0.44 g, eluted first and was recrystallized from hexane to give yellow crystals, mp 120.5°–122° C. NMR ppm (CDCl$_3$) 1.55 (1H, m), 1.7 (2H, m), 2.37 (1H, m), 2.7 (2H, m), 2.95–3.3 (3H, m), 3.9 (2H, m), 8.35 (1H, d), 8.5 (1H, d). Anal. C$_{11}$H$_{13}$Cl$_2$N$_3$ requires C: 51.18; H: 5.07; N: 16.27%. Found C: 51.18; H: 5.28; N: 16.20%. The second component (10), 0.26 g, recrystallized from hexane to give yellow crystals, mp 66°–67° C. NMR ppm (CDCl$_3$) 1.75 (4H, m), 2.75 (2H, m) 3.1 (2H, m), 3.4 (1H, bs), 7.35 (1H, d), 8.25 (1H, d), 8.5 (1H, d). Anal. C$_{11}$H$_{12}$ClN$_3$ requires C: 59.60; H: 5.46; N: 18.95%. Found C: 59.87; H: 5.47; N: 18.68%.

3-(3-Methoxypyrazinyl)-1-azabicyclo[2.2.2]oct-2-ene (11)

A solution of 12 ml of thionyl chloride was cooled to 0° C. as 1.2 g of (7) (0.005 mol) was added. The cooling was removed and the reaction stirred overnight. The solvent was evaporated, the residue treated with ice-water, and the mixture made basic with saturated aqueous K$_2$CO$_3$. The mixture was extracted 3× with 25 ml of CH$_2$Cl$_2$, the extracts washed with brine, dried, and the solvent evaporated. The residue was dissolved in a small amount of methanol and added to a solution of 50 ml of methanol that had reacted with 1 g of Na (0.043 mol). The reaction was heated to reflux for 1 h, the solvent evaporated, the residue treated with ice-water, and the mixture extracted 3× with 25 ml of CH$_2$Cl$_2$. The extracts were washed with brine, dried, and the solvent evaporated. The residue was purified by HPLC eluting with an 8 L gradient beginning with CH$_2$Cl$_2$ and going to 10% methanol-1%NH$_4$OH to give 0.14 g of (11) after recrystallization from hexane, mp 95°–96° C. NMR ppm (CDCl$_3$) 1.57 (2H, m), 1.8 (2H, m), 2.7 (2H, m), 3.05 (2H, m), 3.8 (1H, bs), 4.05 (3H, s), 7.6 (1H, s), 7.95 (1H, d), 8.15 (1H, d). Anal. C$_{12}$H$_{15}$N$_3$O requires C: 66.34; H: 6.96; N: 19.34%. Found C: 66.18; H: 7.09; N: 19.08%.

3-Chloro-3-(3-methoxypyrazinyl)-1-azabicyclo[2.2.2]octane (12)

A solution of 2.4 g of (8) (0.010 mol) in 100 ml of CH$_2$Cl$_2$ was cooled to 0° C. as 2 ml of thionyl chloride in 5 ml of CH$_2$Cl$_2$ was added dropwise. The cooling was removed, the reaction stirred for 1.5 h, then heated to reflux for 45 min. Upon cooling to ambient temperature, ice-water was added to the reaction, followed by enough saturated aqueous K$_2$CO$_3$ to make the reaction basic. The mixture was extracted 3× with 25 ml of CH₂Cl₂, the extracts washed with brine, dried, and the solvent evaporated. The residue was purified by radial chromatography eluting with 2.5% ethanol-0.25% NH₄OH-CHCl₃ to give 1.74 g of (12). Recrystallization from hexane gave colorless crystals, mp 59°-60° C. NMR ppm (CDCl₃) 1.5 (1H, bs), 1.65 (2H, m), 2.35 (1H, m), 2.7 (2H, m) 2.97 (1H, m), 3.15 (2H, m), 3.65 (1H, m), 4.03 (1H, bm), 4.07 (3H, s), 8.1 (2H, m). Anal. $C_{12}H_{16}ClN_3O$ requires C: 56.81; H: 6.36; N: 16.56%. Found C: 56.63; H: 6.41; N: 16.48%. Further elution with 5% ethanol-0.5%NH₄OH-CHCl3 gave 0.13 g of (11), identical to the material produced previously.

3-(3-Methoxypyrazinyl)-1-azabicyclo[2.2.2]octane ethanedioate (13)

A mixture of 0.17 g of (11) (0.00078 mol) and 0.17 g PtO₂ in 50 ml of ethanol was hydrogenated overnight at 60 psi of H₂. The catalyst was removed and the solvent evaporated to give 0.115 g of a clear liquid that crystallized from isopropanol as the oxalate salt (13), 0.07 g, mp 183°-184° C. NMR ppm (D₂O) 1.7 (2H, m), 2.12 (2H, m), 2.5 (1H, m), 3.2-3.6 (5H, m), 4.85 (1H, t), 4.0 (3H, s), 4.05 (1H, m), 8.05 (1H, d), 8.1 (1H, d). Anal. $C_{12}H_{17}N_3O \cdot C_2H_2O_4$ requires C: 54.36; H: 6.19; N: 13.58%. Found C: 54.12; H: 6.31; N: 13.36%.

3-(3-Hexyloxypyrazinyl)-1-azabicyclo[2.2.2]oct-2-ene ethandioate (14)

A solution of 15 ml of thionyl chloride was cooled to 0° C. as 2 g of (7) (0.0088 mol) was added. The cooling was removed and the reaction stirred overnight. The solvent was evaporated, the residue treated with ice-water, and the mixture made basic with saturated aqueous K₂CO₃. The mixture was extracted 3× with 25 ml of CH₂Cl₂, the extracts washed with brine, dried, and the solvent evaporated. The residue was dissolved in a small amount of hexanol and added to a solution of 100 ml of hexanol that had reacted with 1.5 g of Na (0.065 mol). The reaction was heated to 100° C. for 2 h followed by evaporation of the solvent. The remaining hexanol was azeotroped of with water and the residue extracted 3× with 25 ml of CH₂Cl₂. The extracts were washed with brine, dried, and the solvent evaporated to give a brown liquid. Purification by HPLC eluting with an 8 L gradient beginning with CH₂Cl₂ and going to 10% methanol gave 0.55 g of a yellow liquid. NMR ppm (CDCl₃) 0.9 (3H, t), 1.25-1.9 (12H, m), 2.7 (2H, m), 3.05 (2H, m), 3.75 (1H, bs), 4.4 (2H, t), 7.6 (1H, d), 8.15 (1H, d). The oxalate salt (14) crystallized from ethyl acetate, mp 127°-128° C. Anal. $C_{17}H_{25}N_3O \cdot C_2H_2O_4$ requires C: 60.46; H: 7.21; N: 11.13%. Found C: 60.21; H: 6.95; N: 11.36%.

3-(3-Hexyloxypyrazinyl)-1-azabicyclo[2.2.2]octane ethandioate (15)

A mixture of 0.29 g of the free base of (14) (0.001 mol) and 0.15 g PtO₂ in 50 ml of ethanol was hydrogenated overnight at 60 psi of H₂. The catalyst was filtered off and the solvent evaporated to give 0.22 g of a clear liquid. The oxalate salt (15), 0.15 g, crystallized from ethyl acetate as a flocculant colorless solid, mp 137°-138° C. NMR ppm (CDCl₃) 0.9 (3H, t), 1.3-1.55 (6H, m), 1.6-1.9 (4H, m), 2.1 (2H, m), 2.45 (1H, m), 3.25 (1H, m), 3.35-3.65 (4H, m), 3.72 (1H, t), 4.25 (1H, q), 4.35 (2H, t), 8.05 (1H, d), 8.1 (1H, d). Anal. $C_{17}H_{27}N_3O \cdot C_2H_2O_4$ requires C: 60.14; H: 7.70; N: 11.07%. Found C: 60.29; H: 7.91; N: 10.85%.

3-(3-Heptyloxypyrazinyl)-1-azabicyclo[2.2.2]octane hydrochloride (16)

A solution of 10 ml of thionyl chloride was cooled to 0° C. as 1.5 g of (7) (0.0066 mol) was added. The cooling was removed and the reaction stirred overnight. The solvent was evaporated, the residue treated with ice-water, and the mixture made basic with saturated aqueous K₂CO₃. The mixture was extracted 3× with 25 ml of CH₂Cl₂, the extracts washed with brine, dried, and the solvent evaporated. The residue was dissolved in a small amount of heptanol and added to a solution of 100 ml of heptanol that had reacted with 1.5 g of Na (0.065 mol). The reaction was heated to 100° C. for 2 h followed by evaporation of the solvent. The remaining heptanol was azeotroped off with water and the residue extracted 3× with 25 ml of CH₂Cl₂. The extracts were washed with brine, dried, and the solvent evaporated to give a brown liquid. Purification by HPLC eluting with an 8 L gradient beginning with CH₂Cl₂ and going to 10% methanol gave 0.59 g of 3-(3-heptyloxypyrazinyl)-1-azabioyclo[2.2.2]oct-2-ene as a yellow liquid. NMR ppm (CDCl₃) 0.9 (3H, t), 1.25-2.0 (14H, m), 2.95 (2H, m), 3.3 (2H, m), 4.07 (1H, bs), 4.4 (2H, t), 7.65 (1H, s), 8.0 (1H, d), 8.15 (1H, d). A mixture of this material and 0.3 g of PtO₂ in 50 ml of ethanol was hydrogenated overnight at 60 psi of H₂. The catalyst was filtered off and the solvent evaporated. The clear residue was converted to the hydrochloride salt (16), 0.115 g, that crystallized from ethyl acetate, mp 147°-148.5° C. NMR ppm (CDCl₃) 0.9 (3H, t), 1.25-2.9 (12H, m), 2.12 (2H, m), 2.45 (1H, m), 3.22 (1H, m), 3.37 (3H, m), 3.55 (1H, m), 3.72 (1H, m), 4.3 (1H, q), 4.35 (2H, t), 8.02 (1H, d), 8.1 (1H, d). Anal. $C_{18}H_{29}N_3O \cdot HCl$ requires C: 63.60; H: 8.90; N: 12.36%. Found C: 63.44; H: 8.96; N: 12:11%.

3-(3-Butyloxypyrazinyl)-1-azabicyclo[2.2.2]octan-3-ol (18)

To a solution of 40 ml of butanol that had reacted with 0.5 g of Na (0.022 mol) was added 0.78 g of (7) (0.033 mol). The reaction was heated to 60° C. for 1.5 h and the cooled reaction treated with 6 ml of 5 N HCl. The butanol was azeotroped off with water, the residue made basic with saturated aqueous K₂CO₃, and the mixture extracted 3× with 25 ml of CH₂Cl₂. The extracts were washed with brine, dried, and the solvent evaporated to give a yellow solid that was purified by radial chromatography eluting with 5% ethanol-0.5% NH₄OH-CHCl₃ to give 0.55 g of (18) as a yellowish solid. Recrystallization from ether gave a white solid, mp 107°-108° C. NMR ppm (CDCl₃) 1.0 (3H, t), 1.15 (1H, m), 1.35-1.6 (4H, m), 1.85 (2H, m), 2.25 (1H, m), 2.37 (1H, bs), 2.75 (1H, m), 2.82-3.0 (3H, m), 3.05 (1H, m), 3.95 (1H, s), 4.2 (1H, d), 4.45 (2H, q), 8.0 (1H, d), 8.12 (1H, d). Anal. $C_{15}H_{23}N_3O_2$ requires C: 64.96; H: 8.36; N: 15.15%. Found C: 65.21; H: 8.11; N: 15.25%.

3-(3-Butyloxypyrazinyl)-3-chloro-1-azabicyclo[2.2.2]octane hydrochloride (19) and 3-(3-butyloxypyrazinyl)-1-azabicyclo [2.2.2]oct-2-ene hydrochloride (20)

A solution of 2.2 g of (18) in 100 ml of CH₂Cl₂ was cooled to 0° C. as 1.6 ml of thionyl chloride in 5 of CH₂Cl₂ was added dropwise. The cooling was removed and after stirring for 1.5 h the reaction was heated to reflux for 45 min. After the reaction cooled to ambient temperature, ice-water was added to the reaction followed by enough saturated aqueous K₂CO₃ to make the mixture basic. The mixture was extracted 3× with 25 ml of CH$_2$Cl$_2$, the extracts dried, and the solvent evaporated to give a yellow liquid that was purified by radial chromatography eluting with 2.5% ethanol-0.25% NH$_4$OH-CHCl$_3$ give 1.95 g of the free base of (19). NMR ppm (CDCl$_3$) 1.0 (3H, t), 1.5–1.9 (7H, m), 2.37 (1H, m),2.6–2.82 (2H, m), 3.0 (1H, bt), 3.1–3.22 (2H, m), 3.6–4.05 (2H, m), 4.4 (2H, t), 8.05 (2H, m). The hydrochloride salt (19) crystallized from ethyl acetate to give white crystals, mp 140°–141° C. Anal. C$_{15}$H$_{22}$ClN$_3$O-HCl requires C: 54.22; H: 6.98; N: 12.65%. Found C: 54.49; H: 7.10; N: 12.90%. Further elution with 5% ethanol-0.5% NH$_4$OH-CHCl$_3$ gave 0.09 g of the free base of (20) that crystallized from ethyl acetate as the hydrochloride salt (20), mp 156°–157° C. NMR of the free base ppm (CDCl$_3$) 1.0 (3H, t), 1.55 (4H, m), 2.7 (2H, m), 3.05 (2H, m), 3.8 (1H, bs), 4.42 (2H, t), 7.6 (1H, s), 7.95 (1H, d), 8.13 (1H, d). Anal. C$_{15}$H$_{21}$N$_3$O-HCl requires C: 60.91; H: 7.50; N: 14.21%. Found C: 60.98; H: 7.51; N: 14.19%.

3-(3-Butyloxypyrazinyl)-1-azabicyclo[2.2.2]octane hydrochloride (21)

A mixture of 1.7 g of (19), (0.0057 mol) and 0.5 g of 10% Pd on carbon in 50 ml of ethanol was hydrogenated for 1 h at 60 psi of H$_2$. The catalyst was filtered off and the solvent evaporated. The residue was treated with ethanolic HCl and the solvent evaporated. Recrystallization from ethyl acetate gave 1 g of (21), mp 138.5°–139.5° C. NMR ppm (CDCl$_3$) 1.0 (3H, t), 1.45 (2H, m), 1.6–1.9 (5H, m), 2.1 (2H, m), 2.45 (1H, m), 3.15–3.8 (6H, m), 4.28 (1H, q), 4.35 (2H, t), 8.02 (1H, d), 8.1 (1H, d). Anal. C$_{15}$H$_{23}$N$_3$O-HCl requires C: 60.49; H: 8.12; N: 14.11%. Found C: 60.35; H: 8.16; N 13.85%.

3-(3-(3,3,4,4,5,5,6,6,6)Nonafluorohexyloxypyrazinyl)-1-azabicyclo[2.2.2]octan-3-ol hydrochloride (22)

To a solution of 30 ml of 3,3,4,4,5,5,6,6,6-nonafluorohexan-1-ol that had reacted with 0.5 g of Na (0.022 mol) was added 1.63 g of (7) (0.0068 mol). The reaction was heated to 80° C. for 2 h, the reaction cooled to ambient temperature, and 35 ml of 1 N HCl was added. The excess hexanol was azeotroped from the reaction with water and the residue made basic with saturated aqueous K$_2$CO$_3$. The mixture was extracted 3× with 25 ml of CH$_2$Cl$_2$, the extracts washed with brine, and the solvent evaporated. The residue was purified by radial chromatography eluting with 5% ethanol-0.5% NH$_4$OH-CHCl$_3$ and finally with 10% ethanol-1% NH$_4$OH-CHCl$_3$ to give 2.38 g of the free base of (22) as a tan solid. NMR ppm (CDCl$_3$) 1.15 (1H, m), 1.45 (2H, m), 2.22 (1H, m), 2.6–3.0 (6H, m), 3.07 (1H, m), 3.65 (1H, bs), 4.25 (1H, d), 4.8 (2H, m), 8.04 (1H, d), 8.20 (1H, d). The hydrochloride salt (22) crystallized from ethyl acetate, mp 199°–200.5° C. Anal. C$_{17}$H$_{18}$F$_9$N$_3$O$_2$-HCl requires C: 40.53; H: 8.80; N: 8.34%. Found C: 40.72; H: 3.72; N: 8.33%.

3-Chloro-3-(3-(3,3,4,4,5,5,6,6,6)nonafluorohexyloxypyrazinyl)-1-azabicyclo[2.2.2]octane hydrochloride (23) and
3-(3-(3,3,4,4,5,5,6,6,6)nonafluorohexyloxypyrazinyl)-1-azabicyclo[2.2.2]oct-2-ene hydrochloride (24)

A solution of 2 g of the free base of (22) (0.0043 mol) in 100 ml of CH$_2$Cl$_2$ was cooled to 0° C. as 1 ml of thionyl chloride in 5 of CH$_2$Cl$_2$ was added dropwise. The cooling was removed, the reaction stirred 1 h and then heated to reflux for 1 h. After cooling to ambient temperature, the reaction was treated with ice-water and then made basic with saturated aqueous K$_2$CO$_3$. The mixture was extracted 3× with 25 ml of CH$_2$Cl$_2$, the extracts washed with brine, dried, and the solvent evaporated. The residue was purified by radial chromatography eluting with 2.5% ethanol-0.25% NH$_4$OH-CHCl$_3$ to give 1.085 g of the free base of (23). NMR ppm (CDCl$_3$) 1.5 (1H, m), 1.65 (2H, m), 2.35 (1H, m), 2.55-2.82 (4H, m), 2.97 (1H, t), 3.1 (2H, m), 3.62 (1H, bd), 3.92 (1H, m), 4.73 (2H, t), 8.07 (1H, d), 8.15 (1H, d). The hydrochloride salt (23) crystallized from ethyl acetate, mp 160°–161° C. Anal. C$_{17}$H$_{17}$ClF$_9$N$_3$O-HCl requires C: 39.10; H: 3.47; N: 8.04%. Found C: 39.16; H: 3.38; N: 7.86%. Further elution with 5% ethanol-0.5 NH$_4$OH-CHCl$_3$ gave the free base of (24) whose hydrochloride salt (24) crystallized from ethyl acetate, mp 89°–90° C. Anal. C$_{17}$H$_{16}$F$_9$N$_3$O-HCl requires C: 42.03; H: 3.53; N: 8.65%. Found C: 41.80; H: 3.33; N: 8.42%.

3-(3-Pentyloxypyrazinl)-1-azabicyclo[2.2.2]octane hydrochloride (25)

To a solution of 30 ml of pentanol that had reacted with 0.5 g of Na (0.022 mol) was added 1.7 g of (7) (0.0071 mol). The reaction was heated to 70° C. for 2 h, the reaction cooled to ambient temperature, and 30 ml of 1 N HCl was added. The excess pentanol was azeotroped off with water and the residue made basic with 5 N NaOH. The mixture was extracted 3× with 25 ml of CH$_2$Cl$_2$, the extracts washed with brine, dried, and the solvent evaporated. The residue was purified by radial chromatography eluting with 5% ethanol-0.5% N and then with 10% ethanol-1% NH$_4$OH-CHCl$_3$ to give 1.68 g of 3-(3-pentyloxypyrazinyl)-1-azabicyclo[2.2.2]octan-3-ol. NMR ppm (CDCl$_3$) 0.97 (3H, t), 1.2 (1H, m), 1.45 (6H, m), 1.87 (2H, m), 2.3 (1H, m), 2.4 (1H, t), 2.8 (1H, m), 2.93 (3H, m), 3.1 (1H, m), 3.98 (1H, s), 4.28 (1H, d), 4.42 (2H, m), 8.01 (1H, d), 8.11 (1H, d). A solution of 1.48 g of this alcohol (0.0051 mol) in 50 ml of CH$_2$Cl$_2$ was cooled to 0° C. as 1.1 ml of thionyl chloride in 5 ml of CH$_2$Cl$_2$ was added dropwise. The cooling was removed, the reaction stirred 1.5 h and then heated to reflux for 45 min. After cooling to ambient temperature, ice-water was added to the reaction and the reaction made basic with saturated aqueous K$_2$CO$_3$. The mixture was extracted 3× with 25 ml of CH$_2$Cl$_2$, the extracts washed with brine, and the solvent evaporated. The residue was purified by radial chromatography eluting with 5% ethanol- 0.5% N$_4$OH-CHCl$_3$ to give 1.27 g of 3-chloro-3-(3-pentyloxypyrazinyl)-1-azabicyclo[2.2.-2]octane. NMR ppm (CDCl$_3$) 0.99 (3H, t), 1.35–1.8 (7H, m), 1.9 (2H, m) 2.37 (1H, m), 2.6–2.82 (2H, m), 3.0 (1H, t), 3.15 (2H, m), 3.6–4.1 (2H, m), 4.42 (2H, t), 8.06 (2H, m). A mixture of 1.05 g of this chloride (0.0034 mol) and 0.4 g of 10% Pd on carbon in 50 ml of ethanol was hydrogenated 1 h at 60 psi of H$_2$. The catalyst was filtered off, 25 ml of isopropanolic HCl was added, and the solvent was evaporated. The residue was recrystallized from ethyl acetate to give 0.28 g of (25), mp 166°–167° C. NMR ppm (CDCl$_3$) 0.95 (3H, t), 1.41 (4H, m), 1.57–1.9 (5H, m), 2.13 (2H, m), 2.45 (1H, m), 3.12 (1H, m), 3.3–4.46 (3H, m), 3.55 (1H, m), 3.7 (1H, m), 4.3 (1H, q), 4.37 (2H, t), 8.03 (1H, d), 8.1 (1H, d). Anal. C$_{16}$H$_{25}$N$_3$O-HCl requires C: 61.62; H: 8.40; N: 13.47%. Found C: 61.39; H: 8.07; N: 13.48%.

3-(3-Butylthiopyrazinyl)-1-azabicyclo[2.2.2]octane hydrochloride (29)

A 1 g sample of 60% NaH dispersion in oil was triturated twice with hexane then suspended in 300 ml of THF. The mixture was treated with 5 ml of butanethiol and after 30 min the mixture was heated to reflux for 45 min. After cooling to ambient temperature, 1.5 g of (7), (0.0063 mol) was added and the reaction was heated to reflux for 1 h. The mixture was diluted with 100 ml of butanethiol and the reaction was heated to reflux overnight. The solvent was removed by distillation, the residue suspended in 50 ml of $H_2O$, and the mixture extracted 3× with 25 ml of $CHCl_3$, the extracts washed with brine, and the solvent evaporated. The brown solid residue was recrystallized from ether to give 1.25 g of 3-(3-butylthiopyrazinyl)-1- azabicyclo[2.2.2]octan-3-ol (29a). NMR ppm ($CDCl_3$) 0.97 (3H, t), 1.19 (1H, t), 1.19 (1H, m), 1.35-1.57 (4H, m), 1.7 (2H, m), 2.21 (1H, m), 2.5-3.02 (6H, m), 3.2 (2H, m), 4.1 (1H, d), 4.5 (1H, m), 8.17 (1H, d), 8.25 (1H, d). A solution of 1.2 g of (29a) (0.0041 mol) in 100 ml of $CH_2Cl_2$ was cooled to 0° C. as 0.95 ml of thionyl chloride in 10 ml of $CH_2Cl_2$ was added dropwise. The cooling was removed and after 1 h the reaction was heated to reflux for 45 min. After cooling to ambient temperature, the reaction was treated with ice and the solution was made basic with 1 N NaOH. The mixture was extracted 3× with 25 ml of $CH_2Cl_2$, the extracts washed with brine, dried, and the solvent evaporated to give a brown liquid. The liquid was purified by radial chromatography eluting with 5% ethanol-0.5% $NH_4OH$-$CHCl_3$ and then 10% ethanol-1% $NH_4OH$-$CHCl_3$ to give 1 g of 3-chloro-3-(3-butylthiopyrazinyl)-1-azabicyclo[2.2.2]octane (29b). NMR ppm ($CDCl_3$) 0.99 (3H, t), 1.5 (3H, m), 1.7 (4H, m), 2.38 (1H, m), 2.7 (2H, m), 2.98 (1H, m), 3.05-3.4 (4H, m), 3.76 (1H, d), 4.19 (1H, d), 8.18 (1H, d), 8.3 (1H, d). A mixture of 1 g of (29b) (0.0032 mol) and 0.4 g of 10% Pd on carbon in 50 ml of ethanol was hydrogenated for 1 h at 60 psi of $H_2$. The catalyst was removed, the solvent was evaporated, the residue suspended in 5 ml of $H_2O$, and the mixture made basic with saturated aqueous $K_2CO_3$. The mixture was extracted 3× with 25 ml of $CH_2Cl_2$, the extracts dried, and the solvent evaporated. The residue was purified by radial chromatography eluting with 5% ethanol-0.5% $NH_4OH$-$CHCl_3$ and then 10% ethanol-1% $NH_4OH$-$CHCl_3$. The hydrochloride salt (29) crystallized from ethyl acetate to give 0.44 g of a floculant white solid, mp 193°-194° C. NMR ppm ($CDCl_3$) 0.99 (3H, t), 1.5 (2H. m), 1.7 (4H, m), 2.15 (2H, m), 2.5 (1H, m), 3.23 (3H, m), 3.4 (3H, m), 3.64 (2H, m), 4.38 (1H, q), 8.21 (1H, d), 8.31 (1H, d). Anal. $C_{15}H_{23}N_3S$-HCl requires C: 57.40; H: 7.71; N: 13.37%. Found C: 57.14; H: 7.92; N: 13.12%.

3-Pyrazinyl-1-azabicyclo[2.2.2]octane hydrochloride (30) and 3-(3-chloropyrazinyl)-1-azabicyclo[2.2.2]octane hydrochloride (31)

A mixture of 1.175 g of (9), (0.0046 mol), and 0.4 g of 10% Pd on carbon in 50 ml of ethanol was hydrogenated 1 h at 60 psi of $H_2$. The catalyst was removed, the solvent was evaporated, the residue was suspended in 5 ml of $H_2O$, and the mixture made basic with saturated aqueous $K_2CO_3$. The mixture was extracted 3× with $CH_2Cl_2$, the extracts dried, and the solvent was evaporated. The residue was purified by radial chromatography eluting with 10% ethanol-1% N and then with 12.5% ethanol-1.25% $NH_4OH$-$CHCl_3$. The less polar component crystallized from isopropanol as the hydrochloride salt (31), 0.12 g, that contained 0.25 mol of $H_2O$, mp 223° C. dec. NMR of (31) free base ppm ($CDCl_3$) 1.3 (1H, m), 1.55 (1H, m), 1.81 (2H, m), 2.13 (1H, m), 2.74-3.28 (5H, m), 3.55 (1H, t), 3.68 (1H, q), 8.22 (1H, d), 8.48 (1H, d). Anal. $C_{11}H_{14}ClN_3$-HCl-0.25 $H_2O$) requires C: 49.91; H: 15.88; N: 50.05%. Found C: 50.05; H: 5.69; N: 15.42%. The more polar component crystallized from isopropanol as the hydrochloride salt (30), 0.23 g, that contained 0.25 mol of $H_2O$, mp 208°-209° C. dec. NMR of (30) free base ppm ($CDCl_3$) 1.38 (1H, m), 1.57-1.88 (3H, m), 2.08 (1H, m), 2.77-3.3 (6H, m), 3.55 (1H, q), 8.42 (1H, d), 8.5 (1H, s), 8.56 (1H, d). Anal. $C_{11}H_{15}N_3$-HCl-0.25$H_2O$ requires: C: 57.38; H: 7.22; N: 18.25%. Found C: 57.36; H: 7.09; N: 17.84%.

3-(3-Ethoxypyrazinyl)-1-azabicyclo[2.2.2]octane hydrochloride (37)

To a solution of sodium ethoxide prepared from 0.75 g (0.0326 mol) of sodium and 75 ml of anhydrous ethanol was added 1.5 g (0.00625 mol) 3-(3-chloropyrazinyl)-1-azabicyclo[2.2.2]octan-3-ol (7) and the mixture heated to reflux for 1.5 h. The solvent was evaporated, the residue was treated with ice-water, and the mixture extracted 3× with 25 ml of $CH_2Cl_2$. The extracts were washed with brine, dried, and the solvent evaporated to give 1.48 g of yellowish solid. A solution of the solid in 100 ml of $CH_2Cl_2$ was cooled to 0° C. as 1.15 ml of thionyl chloride in 10 ml of $CH_2Cl_2$ was added dropwise. The cooling was removed, the reaction stirred 45 min, and then heated to reflux for 45 min. After cooling to ambient temperature, ice-water was added to the reaction and the mixture made basic with 5N NaOH. The mixture was extracted 3× with 25 ml of $CH_2Cl_2$ and the extracts washed with brine, dried, and the solvent evaporated. The residue was purified by radial chromatography eluting with 5% ethanol/ 0.5% $NH_4OH/CHCl_3$ to give 0.68 g of straw-colored liquid. A mixture of 0.68 g of the liquid and 0.25 g of 10% Pd on carbon in 50 ml of ethanol was hydrogenated 1 h at 60 psi of $H_2$. The catalyst was removed and the solvent was evaporated to give a white solid. The solid was dissolved in ice-water and treated with 3 ml of 1 N NaOH. The mixture was extracted 3× with 25 ml of $CH_2Cl_2$, the extracts dried, and the solvent evaporated. The residue was purified by radial chromatography eluting with 10% ethanol/1% $NH_4OH/CHCl_3$ and the product converted to the hydrochloride salt (37), 0.23 g, 14% yield that crystallized from 2-propanol, mp 237° C. dec. NMR ppm ($CDCl_3$) 1.39 (3H, t), 1.65 (2H, m), 2.0-2.23 (2H, m), 2.41 (1H, m), 3.16-3.58 (5H, m), 3.66-3.75 (1H, m), 4.18-4.28 (1H, m), 4.4 (2H, q), 8.0 (1H, d), 8.07 (1H, d). Anal. $C_{13}H_{19}N_3O$-HCl requires C: 57.88; H: 7.47; N: 15.58%. Found C: 57.96; H: 7.60; N: 15.75%.

3-(3-Propyloxypyrazinyl)-1-azabicyclo[2.2.2]octane hydrochloride (38)

To a solution of sodium propoxide prepared from 0.75 g (0.0326 mol) of sodium and 75 ml of 1-propanol was added 1.5 g (0.00625 mol) (7) and the mixture heated to reflux for 2 h. The solvent was evaporated, the residue was treated with ice-water, and the mixture extracted 3× with 25 ml of $CH_2Cl_2$. The extracts were washed with brine, dried, and the solvent evaporated to give 1.67 g of white solid. A solution of the solid in 100 ml of $CH_2Cl_2$ was cooled to 0° C. as 1.2 ml of thionyl chloride in 5 ml of CH$_2$Cl$_2$ was added dropwise. The cooling was removed, the reaction stirred 45 min, and then heated to reflux for 45 min. After cooling to ambient temperature, ice-water was added to the reaction and the mixture made basic with 5N NaOH. The mixture was extracted 3× with 25 ml of CH$_2$Cl$_2$ and the extracts washed with brine, dried, and the solvent evaporated. The residue was purified by radial chromatography eluting with 5% ethanol/0.5% NH$_4$OH/CHCl$_3$ to give 1.29 g of yellow liquid. A mixture of 1.29 g of the liquid and 0.45 g of 10% Pd on carbon in 50 ml of ethanol was hydrogenated 1 h at 60 psi of H$_2$. The catalyst was removed and the solvent was evaporated to give a white solid. The solid was dissolved in ice-water and treated with 5 ml of 1 N NaOH. The mixture was extracted 3× with 25 ml of CH$_2$Cl$_2$, the extracts dried, and the solvent evaporated. The residue was purified by radial chromatography eluting with 10% ethanol/1% NH$_4$OH/CHCl$_3$ and the product converted to the hydrochloride salt (38), 0.57 g, 32% yield that crystallized from 2-propanol, mp 215°–216° C. dec. NMR ppm (CDCl$_3$) 1.05 (3H, t), 1.59-1.7 (2H, m), 1.8 (2H, m), 2.0-2.23 (2H, m), 2.42 (1H, m), 3.1-3.59 (5H, m), 3.65-3.75 (1H, m), 4.2-4.35 (4H, m), 8.0 (1H, d), 8.06 (1H, d). Anal. C$_{14}$H$_{21}$N$_3$C-HCl requires C: 59.46; H: 7.49; N: 14.86%. Found C: 59.49; H: 7.67; N: 14.83%.

3-(3-Pentylthiopyrazinyl)-1-azabicyclo[2.2.2]octane hydrochloride (39)

A 1 g sample of 60% NaH dispersion in oil was triturated twice with hexane then suspended in 300 ml of THF. The mixture was treated with 5 ml of 1-pentanethiol and after 30 min the mixture was heated to reflux for 30 min. After cooling to ambient temperature, 1.6 g (0.00625 mol) of (7) was added and the reaction heated to reflux for 2 h. Most of the solvent was distilled from the reaction mixture, the residue cooled, and 30 ml of water added. After sitting under vacuum over night, the residue was treated with water and extracted 3× with 50 ml of CH$_2$Cl$_2$. The extracts were dried and the solvent was evaporated to give 1.99 g of slightly yellow solid. A solution of 1.5 g of the solid in 100 ml of CH$_2$Cl$_2$ was cooled to 0° C. as 1.15 ml of thionyl chloride in 10 ml of CH$_2$Cl$_2$ was added dropwise. Cooling was removed and, after 1 h, the reaction was heated to reflux for 1 h. The reaction was treated with ice-water and the mixture made basic with 5N NaOH. The mixture was extracted 3× with 50 ml of CH$_2$Cl$_2$, the extracts washed with brine, dried, and the solvent evaporated. The residue was purified by radial chromatography eluting with 5% ethanol/0.5% NH$_4$OH/CHCl$_3$ to give 1.26 g of a slightly yellow liquid. A mixture of 1.26 g of the liquid and 0.4 g of 10% Pd on carbon in 50 ml of ethanol was hydrogenated 1 h at 60 psi of H$_2$. The catalyst was removed, the solvent evaporated, and the residue dissolved in ice-water and treated with 4 ml of 1 N NaOH. The mixture was extracted 3× with 25 ml of CH$_2$Cl$_2$, the extracts dried, and the solvent evaporated. The residue was purified by radial chromatography eluting with 10% ethanol/ 1% NH$_4$OH/CHCl$_3$ and the product converted to the hydrochloride salt (39), 0.5 g, 30% yield that crystallized from ethyl acetate, mp 219°–220° C. dec. NMR ppm (CDCl$_3$) 0.9 (3H, t), 1.4 (4H, m), 1.70 (4H, m), 2.05-2.3 (2H, m), 2.5 (1H, m), 3.1-3.3 (3H, m), 3.32-3.47 (3H, m), 3.75-3.9 (2H, m), 4.22-4.35 (1H, m), 8.19 (1H, d), 8.29 (1H, d). Anal. C$_{16}$H$_{25}$N$_3$S-HCl requires C: 58.61; H: 7.99; N: 12.81%. Found C: 58.57; H: 8.24; N: 12.58%.

3-(3-Hexylthiopyrazinyl)-1-azabicyclo[2.2.2]octane hydrochloride (40)

A 1 g sample of 60% NaH dispersion in oil was triturated twice with hexane then suspended in 300 ml of THF. The mixture was treated With 5 ml of 1-hexanethiol and after 30 min the mixture was heated to reflux for 30 min. After cooling to ambient temperature, 1.5 g (0.0067 mol) of (7) was added and the reaction heated to reflux for 2 h. Most of the solvent was distilled from the reaction mixture, the residue cooled, and 30 ml of water added. After sitting under vacuum over night, the residue was treated with water and extracted 3× with 50 ml of CH$_2$Cl$_2$. The extracts were dried and the solvent was evaporated to give 1.98 g of slightly yellow solid. A solution of 1.5 g of the solid in 100 ml of CH$_2$Cl$_2$ was cooled to 0° C. as 1.15 ml of thionyl chloride in 10 ml of CH$_2$Cl$_2$ was added dropwise. Cooling was removed and, after 1 h, the reaction was heated to reflux for 1 h. The reaction was treated with ice-water and the mixture made basic with 5N NaOH. The mixture was extracted 3× with 50 ml of CH$_2$Cl$_2$, the extracts washed with brine, dried, and the solvent evaporated. The residue was purified by radial chromatography eluting with 5% ethanol/0.5% NH$_4$OH/CHCl$_3$ to give 1.265 g of a slightly yellow liquid. A mixture of 1.2 g of the liquid and 0.35 g of 10% Pd on carbon in 50 ml of ethanol was hydrogenated 1 h at 60 psi of H$_2$. The catalyst was removed and the solvent was evaporated to give a gray solid. The solid was dissolved in ice-water and treated with 4 ml of 1 N NaOH. The mixture was extracted 3× with 25 ml of CH$_2$Cl$_2$, the extracts dried, and the solvent evaporated. The residue was purified by radial chromatography eluting with 10% ethanol/1% NH$_4$OH/CHCl$_3$ and the product converted to the hydrochloride salt (40), 0.65 g, 40% yield that crystallized from ethyl acetate, mp 181°–183° C. dec. NMR ppm (CDCl$_3$) 0.9 (3H, t), 1.3 (4H, m), 1.45 (2H, m), 1.70 (4H, m) 2.05-2.25 (2H, m), 2.5 (1H, m), 3.1-3.3 (3H, m), 3.3-3.5 (3H, m), 3.55-3.7 (2H, m), 4.2-4.3 (1H, m), 8.19 (1H, d), 8.29 (1H, d). Anal. C$_{17}$H$_{27}$N$_3$S-HCl requires C: 59.71; H: 8.25; N: 12.29%. Found C: 59.43; H: 8.47; N: 12.18%.

EXAMPLE 3

3-(3-Chloropyrazinyl)-1-azabicyclo[2.2.1]heptan-3-ol (26)

A solution of 7.2 ml of 2,2,6,6-tetramethylpiperidine in 300 ml of THF was cooled to −5° C. as 25 ml of 1.6M butyllithium (0.04 mol) in hexane was added dropwise. The reaction was stirred 10 min then cooled to −77° C. as 3 ml of 2-chloropyrazine in 7 ml of THF was added dropwise. After another 15 min, 4.4 g of 1-azabicyclo[2.2.1]heptan-3-one (0.0396 mol) in 10 ml of THF was added and the reaction stirred 1 h. A solution of 8 ml of conc. HCl in 4 ml of ethanol was added and the cooling was removed. When the temperature reached −10° C., 100 ml of water was added, the organics were evaporated, and the residue treated with 11 ml of 5N NaOH. The solvent was reduced to a small volume, ca. 50 ml, the mixture cooled in ice-water, and the solid collected by filtration. The aqueous fraction was extracted 3× with 50 ml of CHCl$_3$, the extracts added to the solid filtrate, and the total volume of the mixture taken to 500 ml with more CHCl$_3$. The mixture was heated to boiling, dried, filtered, and the solvent evaporated to give a brown solid. The solid was recrystallized from isopropanol to give 4.1 g of tan crystalline (26), mp 220° C. dec. NMR ppm (CDCl$_3$) 1.55-1.9 (2H, m), 2.27 (1H, m), 2.42-2.58 (2H, m), 2.75 (2H, m), 2.95 (1H, m), 3.5 (1H, d) 3.6 (1H, d), 8.3 (1H, d) 8.42 (1H, d). Anal. C$_{10}$H$_{12}$ClN$_3$O requires C: 53.22; H: 5.36; N: 18.62%. Found C: 53.10; H: 5.20; N: 18.41%.

Endo-3-(3-hexyloxypyrazinyl)-1-azabicyclo[2.2.2]heptane hydrochlorid hemihydrate (27)

A mixture of 4.8 g of (26) (0.021 mol) and 125 ml of hexanol that had reacted with 1.5 g of Na (0.065 mol) was heated to 80° C. for 45 min. The reaction was cooled to ambient, 100 ml of 1N HCl was added, and the hexanol was azeotroped off with water. The residue was made basic with 1N NaOH and extracted 3× with 50 ml of CH$_2$Cl$_2$. The extracts were washed with brine, dried, and the solvent evaporated to give a dark solid. Recrystallization of the solid from ether gave 3.83 g of 3-(3-hexyloxypyrazinyl)-1-azabicyclo[2.2.1]heptan-3-ol (26a) as a floculent yellow solid. NMR ppm (CDCl$_3$) 0.9 (3H, t), 1.25-1.65 (7H, m), 1.85 (2H, m), 2.25-3.07 (6H, m), 3.1 (1H, d), 3.75 (2H, d), 4.45 (2H, t), 8.01 (1H, d), 8.07 (1H, d). A solution of 1.5 g of (26a) (0.0052 mol) in 75 ml of CH$_2$Cl$_2$ was cooled to 0° C. as 1.1 ml of thionyl chloride in 10 ml of CH$_2$Cl$_2$ was added dropwise. The cooling was removed and after 1.5 h the reaction was heated to reflux for 45 min. The reaction was cooled to ambient, water was added, and the reaction made basic with saturated aqueous K$_2$CO$_3$. The mixture was extracted 3× with 25 ml of CH$_2$Cl$_2$ the washed with brine, dried, and the solvent evaporated to give a yellow oil. Radial chromatography eluting with 2.5% ethanol-0.25% NH$_4$OH-CHCl$_3$ gave 1.2 g 3-chloro-3-(3-hexyloxypyrazinyl)-1-azabicyclo[2.2.1]heptane (26b) as a pinkish liquid. NMR ppm (CDCl$_3$) 0.9 (3H, t), 1.25-1.95 (10H, m), 2.25-3.9 (7H, m), 4.4 (2H, t), 8.0-8.1 (2H, m). A mixture of 1.2 g of (26b) (0.0039 mol) and 0.5 g of 10% Pd on carbon in 50 ml of ethanol was hydrogenated for 1 h at 60 psi H$_2$. The catalyst was removed, the solvent evaporated, the residue suspended in water, and the mixture made basic with saturated aqueous K$_2$CO$_3$. The mixture was extracted 3× with 25 ml of CH$_2$Cl$_2$, the extracts dried, and the solvent evaporated. Tlc shows two major spots, 10% ethanol-1% NH$_4$OH-CHCl$_3$. The less polar of the two component was not well separated. The more polar component was treated with HCl in isopropanol and thoroughly evaporated. The residue was recrystallized from ether to give 0.15 g of (27) as slightly hygroscopic colorless crystals, mp 117°-118° C. NMR ppm (CDCl$_3$) 0.9 (3H, t), 1.25-1.55 (8H, m), 1.85 (3H, m), 3.2-3.75 (6H, m), 4.05 (2H, m), 4.38 (2H, m), 8.05 (1H, d), 8.08 (1H, d). Anal. C$_{16}$H$_{25}$N$_3$O-HCl-0.5H$_2$O requires C: 59.89; H: 8.48; N: 13.10%. Found C: 59.83; H: 8.31; N: 12.95%.

Exo-3-(3-hexyloxypyrazinyl)-1-azabicyclo[2.2.1]heptane hydrochloride (28)

A mixture of 0.35 g of the mixed components from the preparation of (27) (0.0013 mol) and 12 ml of hexanol that had reacted with 0.2 g of Na (0.0087 mol) was heated to 120° C. overnight. The reaction was cooled to ambient temperature, 20 ml of 1N HCl was added, and the hexanol was azeotroped off with water. The residue was made basic with 1N NaOH and the mixture extracted 3× with 25 ml of CH$_2$Cl$_2$. The extracts were dried and evaporated to give 0.33 g of yellow liquid. Tlc shows a two component mixture now highly enriched in the less polar component, 10% ethanol-1% NH$_4$OH-CHCl$_3$. Radial chromatography eluting with 5% ethanol- 0.5% NH$_4$OH-CHCl$_3$ gave 0.2 g of straw colored liquid. The hydrochloride salt (28), 0.15 g, crystallized from ethyl acetate, mp 153°-154° C. NMR ppm (CDCl$_3$) 0.95 (3H, t), 1.25-1.55 (7H, m), 1.82 (2H, m), 1.98 (1H, m), 3.05 (1H, d), 3.15 (1H, d), 3.2-3.7 (7H, mm), 4.22 (1H, m), 4.35 (2H, t), 8.05 (2H, m). Anal. C$_{16}$H$_{25}$N$_3$O-HCl requires C: 61.62; H: 8.40; N: 13.47%. Found C: 61.37; H: 8.31; N: 13.68%.

A reference to the method of generating the 2-chloro-3-lithiopyrazine used in the preparations of (1) and (7) is: Turck, A., Mojovic, L., Queguiner, G. Synthesis 1988,881.

I claim:

1. A compound which is 3-(3-Methoxypyrazinyl)-1,2,5,6-tetrahydro-1-methyl-pyridine or a pharmaceutically-acceptable salt thereof.

2. A compound which is 3-(3-Butyloxypyrazinyl)-1,2,5,6-tetrahydro-1-methyl-pyridine or a pharmaceutically-acceptable salt thereof.

3. A compound which is 3-(3-Hexyloxypyrazinyl)-1,2,5,6-tetrahydro-1-methyl-pyridine or a pharmaceutically-acceptable salt thereof.

4. A compound which is 3-(3-(2-Methoxyethoxy)-pyrazinyl)-1,2,5,6-tetrahydro-1-methylpyridine or a pharmaceutically-acceptable salt thereof.

5. A compound which is 3-(3-Chloropyrazinyl)-1,2,5,6-tetrahydro-1-methylpyridine or a pharmaceutically-acceptable salt thereof.

6. A compound which is 3-(3-Chloropyrazinyl)-1-azabicyclo[2.2.2]oct-2-ene or a pharmaceutically-acceptable salt thereof.

7. A compound which is 3-(3-Methoxypyrazinyl)-1-azabicyclo[2.2.2]oct-2-ene or a pharmaceutically-acceptable salt thereof.

8. A compound which is 3-(3-Methoxypyrazinyl)-1-azabicyclo[2.2.2]octane or a pharmaceutically-acceptable salt thereof.

9. A compound which is 3-(3-Hexyloxypyrazinyl)-1-azabicyclo[2.2.2]oct-2-ene or a pharmaceutically-acceptable salt thereof.

10. A compound which is 3-(3-Hexyloxypyrazinyl)-1-azabicyclo[2.2.2]octane or a pharmaceutically-acceptable salt thereof.

11. A compound which is 3-(3-Heptyloxypyrazinyl)-1-azabicyclo[2.2.2]octane or a pharmaceutically-acceptable salt thereof.

12. A compound which is 3-(3-Heptyloxypyrazinyl)-1,2,5,6-tetrahydro-1-methyl-pyridine or a pharmaceutically-acceptable salt thereof.

13. A compound which is 3-(3-Butyloxypyrazinyl)-1-azabicyclo[2.2.2]oct-2-ene or a pharmaceutically-acceptable salt thereof.

14. A compound which is 3-(3-Butyloxypyrazinyl)-1-azabicyclo[2.2.2]octane or a pharmaceutically-acceptable salt thereof.

15. A compound which is 3-(3-(3,3,4,4,5,5,6,6,6)Nonafluorohexyloxypyrazinyl)-1-azabicyclo[2.2.2]oct-2-ene or a pharmaceutically-acceptable salt thereof.

16. A compound which is 3-(3-Pentyloxypyrazinyl)-1-azabicyclo[2.2.2]octane or a pharmaceutically-acceptable salt thereof.

17. A compound which is Endo-3-(3-hexyloxypyrazinyl)-1-azabicyclo[2.2.1]heptane or a pharmaceutically-acceptable salt thereof.

18. A compound which is Exo-3-(3-hexyloxypyrazinyl)-1-azabicyclo[2.2.1]heptane or a pharmaceutically-acceptable salt thereof.

19. A compound which is 3-(3-Butylthiopyrazinyl)-1-azabicyclo[2.2.2]octane or a pharmaceutically-acceptable salt thereof.

20. A compound which is 3-(3-Chloropyrazinyl)-1-azabicyclo[2.2.2]octane or a pharmaceutically-acceptable salt thereof.

21. A compound which is 3-(3-Ethoxypyrazinyl)-1,2,5,6-tetrahydro-1-methylpyridine or a pharmaceutically-acceptable salt thereof.

22. A compound which is 3-(3-Propyloxypyrazinyl)-1,2,5,6-tetrahydro-1-methyl-pyridine or a pharmaceutically-acceptable salt thereof.

23. A compound which is 3-(3-Pentyloxypyrazinyl)-1,2,5,6-tetrahydro-1-methyl-pyridine or a pharmaceutically-acceptable salt thereof.

24. A compound which is 3-(3-Hexylthiopyrazinyl)-1,2,5,6-tetrahydro-1-methyl-pyridine or a pharmaceutically-acceptable salt thereof.

25. A compound which is 3-(3-Pentylthiopyrazinyl)-1,2,5,6-tetrahydro-1-methyl-pyridine or a pharmaceutically-acceptable salt thereof.

26. A compound which is 3-(3-Ethoxypyrazinyl-1-azabicyclo[2.2.2]octane or a pharmaceutically-acceptable salt thereof.

27. A compound which is 3-(3-Propyloxypyrazinyl)-1-azabicyclo[2.2.2]octane or a pharmaceutically-acceptable salt thereof.

28. A compound which is 3-(3-Pentylthiopyrazinyl)-1-azabicyclo[2.2.2]octane or a pharmaceutically-acceptable salt thereof.

29. A compound which is 3-(3-Hexylthiopyrazinyl)-1-azabicyclo[2.2.2]octane or a pharmaceutically-acceptable salt thereof.

30. A pharmaceutical composition for stimulating the cognitive functions of the forebrain and hippocampus, comprising an effective amount of a compound according to any of claims 1-29 together with a pharmaceutically-acceptable carrier or diluent.

31. The pharmaceutical composition according to claim 30 in the form of an oral dosage unit or a parenteral dosage unit.

32. The pharmaceutical composition according to claim 31, wherein said dosage unit comprises about 1 to about 100 mg of the compound.

33. A method of stimulating the cognitive functions of the forebrain and hippocampus, comprising administering an effective amount of a compound according to any of claims 1-29.

34. A method of stimulating the cognitive functions of the forebrain and hippocampus comprising administering to a subject in need a pharmaceutical composition according to claim 30.

35. The method according to claim 34, wherein said pharmaceutical composition is in the form of an oral dosage unit, or an parenteral dosage unit.

* * * * *

UNITED STATES PATENT AND TRADEMARK OFFICE
CERTIFICATE OF CORRECTION

PATENT NO. : 5,182,283
DATED : January 26, 1993
INVENTOR(S) : Ward

It is certified that error appears in the above-indentified patent and that said Letters Patent is hereby corrected as shown below:

Col. 1, line 55
    (Formula I)
and
Col. 3, line 5
    (Formula I):    change    "    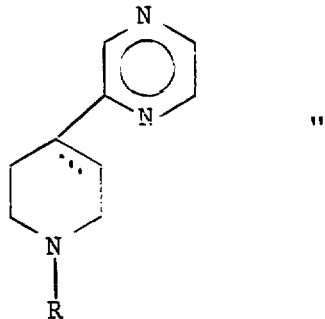    "

to    --    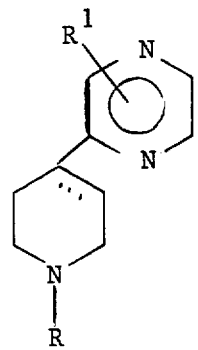    --

Signed and Sealed this

Third Day of October, 1995

Attest:

BRUCE LEHMAN

Attesting Officer    Commissioner of Patents and Trademarks